US00PP27753P3

(12) United States Plant Patent
Marczynski

(10) Patent No.: US PP27,753 P3
(45) Date of Patent: Mar. 7, 2017

(54) ***CLEMATIS* PLANT NAMED 'VIVA POLONIA'**

(50) Latin Name: ***Clematis* hybrid**
Varietal Denomination: VIVA POLONIA

(71) Applicant: Szczepan Marczynski, Pruszkow (PL)

(72) Inventor: Szczepan Marczynski, Pruszkow (PL)

( * ) Notice: Subject to any disclaimer, the term of this patent is extended or adjusted under 35 U.S.C. 154(b) by 118 days.

(21) Appl. No.: 14/544,376

(22) Filed: Dec. 29, 2014

(65) Prior Publication Data

US 2016/0192557 P1 Jun. 30, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

Bourne. What new plants will steal the show at Chelsea, The Telegraph retrieved on Jun. 16, 2016, retrieved from the Internet at <http://www.telegraph.co.uk/gardening/chelseaflowershow/10831436/What-new-plants-will-steal-the-show-at-Chelsea.html> 2014, 7 pp.*

* cited by examiner

*Primary Examiner* — June Hwu
(74) *Attorney, Agent, or Firm* — Cassandra Bright

(57) ABSTRACT

A new and distinct *Clematis* hybrid named 'VIVA POLONIA' is disclosed, characterized by extremely floriferous, medium deep magenta colored flowers with distinctive white centers and tepal bases. Plants have a long blooming period and compact growth. The new cultivar is a *Clematis* typically suited for ornamental container and landscape use.

1 Drawing Sheet

Latin name of the genus and species: *Clematis* hybrid.
Variety denomination: 'VIVA POLONIA'.

BACKGROUND OF THE INVENTION

The new *Clematis* cultivar is a product of a planned breeding program conducted by the inventor, Szczepan Marczynski, in Pruszkow, Poland. The objective of the breeding program was to produce new compact *Clematis* varieties with novel or new colors. The cross resulting in this new variety was made during 2004.

The seed parent is the unpatented variety, *Clematis* 'Matka Siedliska'. The pollen parent is the unpatented variety, *Clematis* 'Warszawska Nike'. The new variety was identified as a potentially interesting selection in 2006, at a greenhouse in Pruszkow, Poland.

Asexual reproduction of the new cultivar 'VIVA POLONIA' by vegetative tip cuttings was first performed during 2007, at a greenhouse in Pruszkow, Poland. Subsequent propagation has shown that the unique features of this cultivar are stable and reproduced true to type in 8 successive generations.

SUMMARY OF THE INVENTION

The cultivar 'VIVA POLONIA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'VIVA POLONIA.' These characteristics in combination distinguish 'VIVA POLONIA' as a new and distinct *Clematis* cultivar:

1. Extremely floriferous plants, with plants covered in flowers at maturity.
2. Medium sized flowers
3. Free flowering habit.
4. Compact plant growth, reaching 1.5 to 2 meters tall.
5. Long blooming period.
6. Flowers in a deep magenta red/claret color with attractive white shading and white tepal base.

PARENTAL COMPARISON

Plants of the new cultivar 'VIVA POLONIA' are similar to plants of the seed parent in most horticultural characteristics, however, plants of the new cultivar 'VIVA POLONIA' differ in the following:

1. Flowers are a deep red magenta color with white shading and white tepal base. The seed parent has white flowers with pink shading.
2. Single flower. The seed parent is single flower on new growth and double flower on previous year's growth.
3. Smaller flowers than seed parent.

Plants of the new cultivar 'VIVA POLONIA' are similar to plants of the pollen parent, in most horticultural characteristics, however, plants of the new cultivar 'VIVA POLONIA' differ in the following;

1. Flowers in a deep red magenta color with white shading and white base. The pollen parent has solid purple-violet flowers.

COMMERCIAL COMPARISON

Plants of the new cultivar 'VIVA POLONIA' can be compared to the known commercial variety *Clematis* hybrid 'Solidarnosc', unpatented. The *Clematis* varieties have similar flower color and produce similar amounts of tepals. 'VIVA POLONIA' differs from 'Solidarnosc' in the following:

1. Flowers in a deep magenta red/claret color with white shading and white tepal base. The comparator has solid red flowers with occasional faint, light pink streaking.
2. Ovate tepals. The comparator has elliptic shaped tepals.
3. More floriferous than comparator.

Plants of the new cultivar 'VIVA POLONIA' can be compared to the known commercial variety *Clematis* 'Sweet Summer Love' U.S. Plant Pat. No. 24,044. The *Clematis* varieties have similar flower color and produce similar amounts of tepals. 'VIVA POLONIA' differs from the comparator in the following:

1. Six to eight tepals. The comparator has 4 tepals
2. Larger flower size.
3. Flower color is near RHS Red-purple 71A. The comparator flower color is near RHS Red-purple 61A.

BRIEF DESCRIPTION OF THE PHOTOGRAPH

The accompanying photograph in FIG. 1 illustrates in full color typical flowers and foliage of 'VIVA POLONIA' grown outdoors in Pruszkow, Poland. This plant is approximately 3 years old, grown outdoors.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1995, except where general terms of ordinary dictionary significance are used. The following observations and measurements describe 'VIVA POLONIA' plants grown outdoors in Pruszkow, Poland. The growing temperature ranged from approximately 15° C. to 18° C. at night to 18° C. to 27° C. during the day. No artificial light, photoperiodic treatments or chemical treatments were given to the plants. Measurements and numerical values represent averages of typical flowering types.

Botanical classification: *Clematis* hybrid 'VIVA POLONIA'.

Age of the plant described: Approximately 3 years old.

PROPAGATION

Typical method: Stem cuttings.

Time to initiate rooting: Approximately 10 days at 18-24° C.

Time to produce a rooted plantlet: 20-30 days at 18-24° C.

Root description: Moderate density, moderate branching, and medium thickness, fleshy in texture.

Root color: Near RHS Grey-orange 163A and 163B, both colors present individually, and blended together.

Root diameter: 100-150 CM.

PLANT

Growth habit: Perennial climbing vine.

Height: Approximately 150 to 200 cm.

Plant spread: Approximately 150-200 cm.

Crop time to flower: 1-2 years.

Growth rate: 150-200 cm per year.

Branching characteristics: Opposite facing, basal branching.

Length of stem: Basal; 150-200 cm. side Branches 45-55 cm.

Diameter of stem: Approximately 0.2 to 0.4 cm.

Stem color: Young, near RHS Yellow-green 144A, sunny side slightly pinkish near RHS Red-purple 70A. Mature, near RHS Greyed-orange 175A.

Lateral stem texture: Ribbed.

Number of lateral branches: Basal branches; 12, side branches: 8.

Number of leaves per lateral branch: 20 to 30.

Internode length: On basal 10-11 cm, on side branches 5-7 cm.

FOLIAGE

Leaf:

*Arrangement.*—Opposite, single and ternate.

*Quantity of leaflets per leaf.*—1-3.

*Overall leaf length.*—Average 10-20 cm.

*Overall leaf diameter.*—Average 3-15 cm.

*Shape of blade.*—Heart shaped, entire some 2 and 3 lobed.

*Apex.*—Acute.

*Base.*—Rounded.

*Attachment.*—Stalked.

*Margin.*—Entire.

*Texture of both surfaces.*—Glabrous, matte.

*Color.*—Young foliage upper side: Near a mixture of RHS Yellow-green 144B and 144C. Young foliage under side: Near RHS Yellow-green 144B. Mature foliage upper side: Near RHS Yellow-green 147A. Mature foliage under side: Near RHS Yellow-green 147B.

*Venation.*—Type: Palmate. Venation color upper side: Near RHS Yellow-green 144A. Venation color under side: Near RHS Yellow-green 146C.

Petiole:

*Length.*—Average range 4-5 cm.

*Diameter.*—Approximately 0.1 cm.

*Texture.*—Glabrous.

*Color.*—Upper: Near RHS Red-purple 59A. Lower: Near RHS Yellow-green 144C.

FLOWER

Bloom period:

*Natural season.*—Late Spring to Summer. June through July free flowering abundantly. September a second flowering occurs, with less flowers.

Flower type: Single, rotate flower with tepals overlapping. Flowering occurring on both previous year's growth and current year's growth.

Flower aspect: Upward or outward facing.

Rate of flower opening: Approximately 1-2 days from bud to fully opened flower.

Flower longevity on plant: Approximately 10-14 days, after fully opened. Partly self-cleaning.

Quantity of flowers per lateral stem: 4-12.

Quantity of flowers buds per lateral stem: 20-40.

Quantity of flowers per plants: About 350.

Flower size:

*Diameter.*—Average 12-15 cm.

*Depth.*—Average 7.0 cm.

Calyx shape: Outspread and rotate.

Tepal:

*Tepal shape.*—Ovate.

*Number of tepals.*—6-8.

*Texture.*—Velvety, upper and lower surfaces.

*Tepal appearance.*—Velvety, somewhat matte.

*Tepal arrangement*.—Rotate, partly overlapping.
*Tepal margin*.—Entire, undulate.
*Tepal tip*.—Apiculate.
*Tepal base*.—Cuneate.
*Tepal length*.—6.0-7.5 cm.
*Tepal width*.—3.0-4.5 cm.

Color:

*Tepals: When opening*.—Upper surface: Near RHS Red-purple 71A with center streaks near White N155A. Center streak is strong at base, fading until apex. Little or no white streak at apex. Lower surface: Near RHS Red-purple 70A on margins (edges), 70C in central part with shading near White N155A, ribs 70A, Yellow-green 144C between ribs.

*Fully opened*.—Upper surface: Near RHS Red-purple 71A with White N155A center and base. Stronger white streak than immature flowers. White streak is very strong at base, becoming lighter towards apex. Lower surface: Near RHS Red-purple 70A on margins (edges), 70C in central part with shades of White N155A, ribs 70A, Yellow-green 144C between ribs.

Bud:

*Shape*.—Narrow ovate.
*Length*.—Approximately 4-6 cm.
*Diameter*.—Approximately 1-2 cm.
*Color*.—Near RHS Green 137D with narrow stripes of Red-purple 61A.

Peduncle:

*Length*.—Average range 7-8.5 cm.
*Diameter*.—Approximately 0.2 cm.
*Strength*.—Stiff.
*Color*.—Near RHS Greyed-Purple 187A.

Fragrance: None.

REPRODUCTIVE ORGANS

Stamens:

*Number*.—Average 60-80 per flower.
*Anther length*.—Approximately 0.5 cm.
*Anther color*.—Near RHS Red-purple 59A.
*Anther shape*.—Oblong.
*Filament length*.—Approximately 0.6 cm.
*Filament color*.—Near RHS Yellow 4D.
*Pollen quantity*.—Medium.
*Pollen color*.—Near RHS Grey-green 188C.

Pistil:

*Number*.—60-70.
*Length*.—Approximately 1-1.2 cm.
*Style length*.—Approximely 0.5 cm.
*Style color*.—Near RHS Yellow-green 144C.
*Stigma*.—Shape: Rounded. Color: Near RHS Yellow-Green 150B.
*Ovary color*.—Near RHS Yellow-green 150B.

OTHER CHARACTERISTICS

Seeds:

*Quantity of seeds*.—40-50.
*Seed length*.—2-2.5 cm.
*Seed diameter*.—0.3-0.4 cm.
*Seed color*.—Immature: Near RHS Yellow-green 145A. Mature: Between Near RHS Greyed-orange 164A-166B.

Disease/pest resistance: Neither resistance nor susceptibility to normal diseases and pests of *Clematis* has been observed.

Lowest temperature tolerant to: USDA Zones 4 through 9.

What is claimed is:

1. A new and distinct cultivar of *Clematis* hybrid plant named 'VIVA POLONIA' as herein illustrated and described.

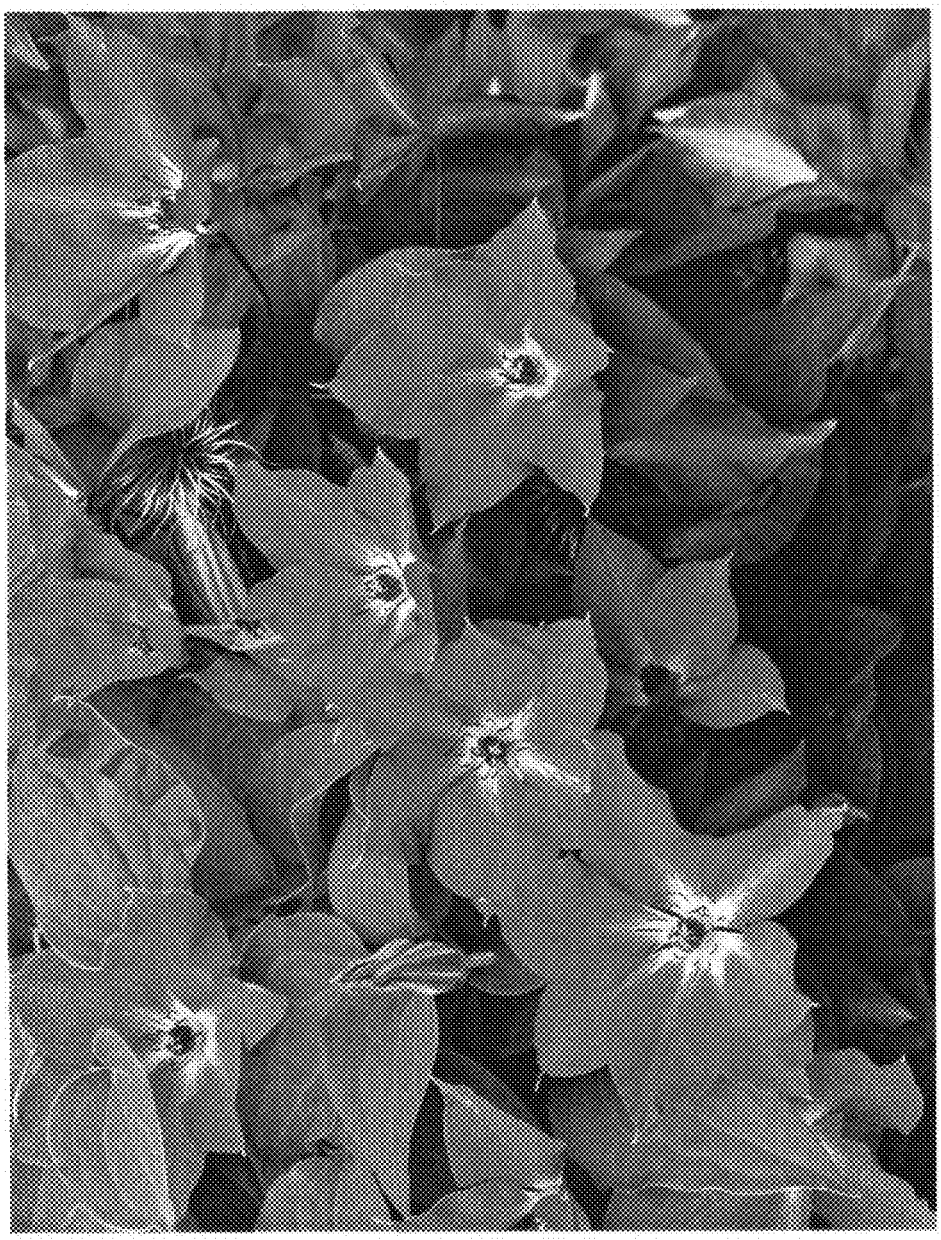

* * * * *